(12) United States Patent
De Wijs et al.

(10) Patent No.: US 10,517,636 B2
(45) Date of Patent: Dec. 31, 2019

(54) TRANSDUCER TRANSFER STACK

(71) Applicant: KONINKLIJKE PHILIPS N.V., Eindhoven (NL)

(72) Inventors: Willem-Jan Arend De Wijs, Oss (NL); Johannes Wilhelmus Weekamp, Beek en Donk (NL); Cornelis Gerardus Visser, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 133 days.

(21) Appl. No.: 15/580,744

(22) PCT Filed: Jun. 15, 2016

(86) PCT No.: PCT/EP2016/063712
§ 371 (c)(1),
(2) Date: Dec. 8, 2017

(87) PCT Pub. No.: WO2016/207041
PCT Pub. Date: Dec. 29, 2016

(65) Prior Publication Data
US 2018/0146981 A1 May 31, 2018

(30) Foreign Application Priority Data
Jun. 24, 2015 (EP) .................................. 15173652

(51) Int. Cl.
*A61B 17/34* (2006.01)
*G01N 29/24* (2006.01)
(Continued)

(52) U.S. Cl.
CPC ........ *A61B 17/3403* (2013.01); *B06B 1/0688* (2013.01); *G01N 29/2437* (2013.01);
(Continued)

(58) Field of Classification Search
CPC ..... B06B 1/0688; B06B 1/00; B06B 2201/56; B06B 2201/76; H01L 41/45;
(Continued)

(56) References Cited

U.S. PATENT DOCUMENTS 3,984,903 A * 10/1976 Murayama ............ B06B 1/0688
29/25.35
6,049,958 A 4/2000 Eberle
(Continued)

FOREIGN PATENT DOCUMENTS

CN 1618530 A 5/2005
JP 2003347568 A 12/2003
(Continued)

OTHER PUBLICATIONS

Zhuang, Xuefeng et al "Fabrication of Flexible Transducer Arrays with Through-Wafer Electrical Interconnects based on Trench Refilling with PDMS", Journal of Microelectromechanical Systems, vol. 17, No. 2, Apr. 2008.
(Continued)

*Primary Examiner* — Patricia L. Nordmeyer

(57) ABSTRACT

The invention relates to a transfer stack (TS) for transferring a portion of a foil within a perimeter (P) that includes a transducer (T) to an article (A) such as a medical device or a medical needle. The transfer stack includes a carrier substrate (CS), a foil (F) having a transducer (T) incorporated therein, and the transducer is laterally surrounded by a perimeter (P). The foil (F) is separable from the carrier substrate (CS) by overcoming a first peel retaining force (PRF1). An adhesive layer (AL) is also attached to the foil. The adhesive layer (AL) is configured to provide adhesion between the foil (F) and an article (A) such that when the article (A) is attached to the foil via the adhesive layer (AL) the foil (F) is separable from the surface of the article (A) by overcoming a second peel retaining force (PRF2). The
(Continued)

second peel retaining force (PRF2) is greater than the first peel retaining force (PRF1).

23 Claims, 7 Drawing Sheets

(51) Int. Cl.
  *B06B 1/06* (2006.01)
  *A61B 17/00* (2006.01)
(52) U.S. Cl.
  CPC ............... *A61B 2017/00526* (2013.01); *A61B 2017/3413* (2013.01); *B06B 2201/56* (2013.01); *B06B 2201/76* (2013.01)
(58) Field of Classification Search
  CPC ... H01L 41/257; H04R 17/005; H04R 31/006; Y10T 29/42; Y10T 29/4981; Y10T 428/14; Y10T 428/15; B31D 1/028; A61B 17/3403; A61B 2562/125; A61B 2017/3413; A61B 2017/00526; G01N 29/2437
  See application file for complete search history.

(56) References Cited

U.S. PATENT DOCUMENTS

| | | | |
|---|---|---|---|
| 6,217,518 B1 | 4/2001 | Holdaway | |
| 2003/0136503 A1 | 7/2003 | Green | |
| 2010/0087782 A1 | 4/2010 | Ghaffari | |
| 2010/0200538 A1 | 8/2010 | Petisce | |
| 2010/0298895 A1 | 11/2010 | Ghaffari | |
| 2014/0024945 A1 | 1/2014 | Mung | |
| 2015/0126834 A1 | 5/2015 | Wang | |

FOREIGN PATENT DOCUMENTS

| | | |
|---|---|---|
| WO | 2013043906 A1 | 3/2013 |
| WO | 2013090689 A1 | 6/2013 |
| WO | 2013174609 A1 | 11/2013 |
| WO | 2015155645 A1 | 10/2015 |

OTHER PUBLICATIONS

Papkovsky, Dmitri B. et al "Quality Assessment of Packaged Foods by Optical Oxygen Sensing", Proc. SPIE 5996, Optical Sensors and Sensing Systems for Natural Resources and Food Safety and Quality, vol. 5996, Nov. 2005.

Schiavone, Giuseppe et al "Advanced Electrical Array Interconnections for Ultrasound Probes Integrated in Surgical Needles", IEEE 16th Electronics Packaging Technology Conference, 2014.

\* cited by examiner

TRANSDUCER TRANSFER STACK

CROSS-REFERENCE TO PRIOR APPLICATIONS

This application is the U.S. National Phase application under 35 U.S.C. § 371 of International Application No. PCT/EP2016/063712, filed on Jun. 15, 2016, which claims the benefit of European Patent Application No. 15173652.7, filed on Jun. 24, 2015. These applications are hereby incorporated by reference herein.

FIELD OF THE INVENTION

The present invention relates to the transducer assembly field in general and may be used to attach a transducer to an article. More particularly it relates to the attachment of a piezoelectric transducer to a medical device and may be used for example to attach a piezoelectric ultrasound transducer to a medical needle.

BACKGROUND OF THE INVENTION

Advances in techniques such as micromachining and planar processing have enabled the manufacture of a wide variety of transducers which can be used in all fields of industry ranging from electronic devices, optics, biotechnology, solar to the medical device field. These transducers, which include ultrasound, thermal, optical and mechanical devices, have enabled a vast array of sensing and energy conversion applications. Conventionally the transducers used in such applications are made separately to the device in which they are ultimately used. A need therefore exists for a method for attaching transducers to the devices in which they are used. One example of this need arises in the medical device field as described in currently unpublished PCT application PCT/IB2015/052425. In this, a piezoelectric sensor that is manufactured using lamination and deposition processes must be attached to a medical device for use in an ultrasound-based tracking application. This need may be aggravated by the need to transfer an essentially planar device to a curved surface, such as the shaft of a catheter or needle.

A document "Fabrication of Flexible Transducer Arrays With Through-Wafer Electrical Interconnects Based on Trench Refilling With PDMS" by Xuefeng Zhuang et al, JOURNAL OF MICROELECTROMECHANICAL SYSTEMS, VOL. 17, NO. 2, APRIL 2008 discloses a technique for wrapping a flexible transducer array around a catheter tip for use in a side-looking ultrasound imaging application. The disclosed technique includes the construction of flexible capacitive micromachined ultrasonic transducer (CMUT) arrays by forming polymer-filled deep trenches in a silicon substrate. Tweezers are subsequently used to wrap the flexible transducer around the circular cross section of the catheter tip.

Document US2010/0200538A1 discloses the fabrication of an analyte sensor component that includes an inorganic substrate having deposited thereon a release layer, a first flexible dielectric layer and a second flexible dielectric layer insulating there between electrodes, contact pads and traces connecting the electrodes and the contact pads of a plurality of sensors. Openings are provided in one of the dielectric layers over one or more of the electrodes to receive an analyte sensing membrane for the detection of an analyte of interest and for electrical connection with external electronics. The plurality of fabricated sensor components are lifted off the inorganic substrate.

Document US2015/0126834A1 relates to the fabrication of electrochemical biosensors and chemical sensors. An epidermal biosensor includes an electrode pattern that is formed on a coated surface of a paper-based substrate to provide an electrochemical sensor. The electrode pattern includes an electrically conductive material and an electrically insulative material configured in a particular design layout. An adhesive sheet is attached on a surface of the electrochemical sensor having the electrode pattern, the adhesive sheet capable of adhering to skin or a wearable item, in which the electrochemical sensor, when attached to the skin or the wearable item, is operable to detect chemical analytes within an external environment.

The present invention seeks to address drawbacks of the above and other known solutions to this and related needs.

SUMMARY OF THE INVENTION

It is an object of the present invention to provide an apparatus and method for attaching a transducer to an article. Thereto a method and a device are provided as defined in the independent claims.

In accordance with one aspect of the invention a transfer stack TS for transferring a portion of a foil within a perimeter P that includes a transducer T to an article A is provided. The article may be a medical device such as a catheter, a cannula, or a needle, and the transfer stack is particularly suited for transferring a transducer to a curved surface. However, the transfer stack is also useful for attaching the portion of foil that includes the transducer to articles in general, irrespective of their surface topography. The transfer stack includes a carrier substrate CS, a foil F comprising a transducer T that is laterally surrounded by a perimeter P, and an adhesive layer AL. A first surface S1 of the foil F is attached to the carrier substrate, and the adhesive layer AL is attached to the second surface S2 of the foil F. The first surface S1 of the foil F is separable from the carrier substrate CS by applying in a direction normal to the carrier substrate CS and at an edge EF1, EF2 of the foil F a peeling force that overcomes a first peel retaining force PRF1. The adhesive layer AL provides adhesion between the foil F and the article A such that when the article A is attached to the foil via the adhesive layer AL the second surface S2 of the foil F is separable from the surface of the article A by applying in a direction normal to the surface of the article A and at the edge EF1, EF2 of the foil F a peeling force that overcomes a second peel retaining force PRF2. Moreover, the second peel retaining force PRF2 is greater than the first peel retaining force PRF1. Thus, a transfer stack is provided in which a transducer-bearing foil has on one surface S2 an adhesive layer that requires greater force to peel it from an article than is required to peel it from the carrier substrate. Moreover, the foil F is cut along at least a portion of the perimeter P that includes the transducer T such that when the article A is attached to the foil and subsequently peeled in a direction normal to the carrier substrate CS the portion of the foil within the perimeter P becomes separated from the carrier substrate at the perimeter P by overcoming the first peel retaining force PRF1 and the portion of the foil within the perimeter P remains attached to the article A. By providing a cut along the perimeter P the portion of the foil including the perimeter is isolated from the foil, thereby allowing only this portion, including the transducer, to be transferred to the article. Because the second peel retaining force PRF2 is greater than the first peel retaining force PRF1, when the article is e.g. pressed into the adhesive layer AL and the article A is subsequently pulled away from the carrier substrate CS, the portion of the foil F within the perimeter P is separated from the carrier substrate CS and remains attached to the article A. The portion of the foil F within the perimeter P may alternatively be separated from the carrier substrate CS by rolling the article A along the surface of the adhesive layer AL.

In accordance with another aspect of the invention the adhesive layer AL further comprises a removable outer liner layer ROL. The removable outer liner layer ROL acts to protect the adhesive layer during assembly of the transfer stack, and prior to its attachment to an article. Moreover in some embodiments the removable outer liner layer may be present only outside the perimeter P. This improves the ease of transfer of the portion of the foil within the perimeter P to the article A by allowing the material outside the perimeter P to remain attached to the carrier substrate CS and therefore preventing its transfer to the article A. The ROL layer is however not essential since it is also possible to transfer the portion of the foil within the perimeter P to the article A by e.g. attaching an article A with a contact surface area that corresponds to that of perimeter P, or by removing the adhesive layer AL, or by removing the adhesive layer AL and the foil outside perimeter P prior to attachment of the article A.

In accordance with another aspect of the invention the transfer stack TS is further provided with a support substrate SS that is attached to the carrier substrate CS. Moreover, the support substrate SS is formed from a material having an indentation hardness value that exceeds the indentation hardness value of the carrier substrate CS. The increased indentation hardness provided by the support substrate as compared to that of the carrier substrate facilitates improved bonding, specifically improved uniformity of bonding, between the foil and the carrier substrate during assembly of the transfer stack. The support substrate SS also provides a rigidity that allows alignment of transducer T within perimeter P during assembly of the stack, and facilitates easier handling and transport.

In accordance with another aspect of the invention the interface between the adhesive layer AL and the foil F defines an adhesive layer-foil interface ALFI. Moreover the interface between the foil F and the carrier substrate CS defines a foil-carrier substrate interface FCSI. The extent of the adhesive layer-foil interface ALFI extends beyond the perimeter P. In other words a continuous adhesive layer is provided within, and extending beyond the perimeter P. This improves the bonding between the portion of foil within perimeter and the article. Furthermore, the extent of the adhesive layer-foil interface ALFI is within the extent of the foil-carrier substrate interface FCSI such that there are gaps GALF1, GALF2 between the edges EAL1, EAL2 of the adhesive layer AL and the edges of the foil EF1, EF2. The gaps GALF1, GALF2 improve the resistance of the foil to peeling at the foil edges EF1, EF2 during handling and assembly of the transfer stack.

In accordance with another aspect of the invention a transfer stack is defined in which the interface between the adhesive layer AL and the foil F defines an adhesive layer-foil interface ALFI, and in which the interface between the foil F and the carrier substrate CS defines a foil-carrier substrate interface FCSI. Moreover the extent of the adhesive layer-foil interface ALFI extends beyond the perimeter P, and the extent of the adhesive layer-foil interface ALFI is within the extent of the foil-carrier substrate interface FCSI such that there are gaps GALF1, GALF2 between the edges EAL1, EAL2 of the adhesive layer AL and the edges of the foil EF1, EF2. Moreover the transfer stack includes a support substrate SS that has a planar surface with a boundary BSS that contacts the foil F, and the carrier substrate (CS) is in the form of a layer. Furthermore the foil-carrier substrate interface FCSI extends beyond the boundary of the planar surface of the support substrate BSS. Thus, a transfer stack is defined in which a carrier substrate layer and the foil are essentially wrapped around the edges of the support substrate. The edges may be the edges of the support substrate surface that face towards the transducer, or those on the reverse side of the support substrate that face away from the transducer. By wrapping the carrier substrate layer and the foil beyond either of these edges the stability of the transfer stack during its assembly, and the resistance to de-lamination during handling is improved. This is particularly advantageous in embodiments where the adhesive layer A further comprises a removable outer liner layer ROL because its removal prior to attaching the article to the adhesive layer risks causing de-lamination.

In accordance with another aspect of the invention the portion of the foil F within the perimeter P is attached to an article. The article may for example be a medical device such as a catheter, a cannula, a needle, or a surgical tool, although this portion may be attached to other articles in general.

In accordance with another aspect of the invention a method of attaching the portion of the foil F within the perimeter P to an article A is disclosed. The article may be a medical device such as a medical needle. According to the method the article is either pressed into the adhesive layer, or rolled along the surface of the adhesive layer in order to attach the portion to the article. Attachment is facilitated by the cut along at least a portion of the perimeter P. The cut reduces the normally-applied force that is required to peel the portion of the foil within the perimeter; i.e. towards the magnitude required to overcome the first peel retaining force PRF1.

DETAILED DESCRIPTION OF THE INVENTION

As described above, the present invention provides a transfer stack TS for transferring a portion of a foil within a perimeter P that includes a transducer T to an article A. An article comprising the portion, a method of forming the transfer stack, and a method of attaching the portion of the foil F within the perimeter P to an article are also disclosed.

The transfer stack and associated methods find application in particular in the medical field where it is desirable to be able to attach transducers, i.e. sensors or actuators to medical devices. Whilst the transfer stack finds application in the medical field it also finds wider application in the transducer field in general.

Figure 1A:
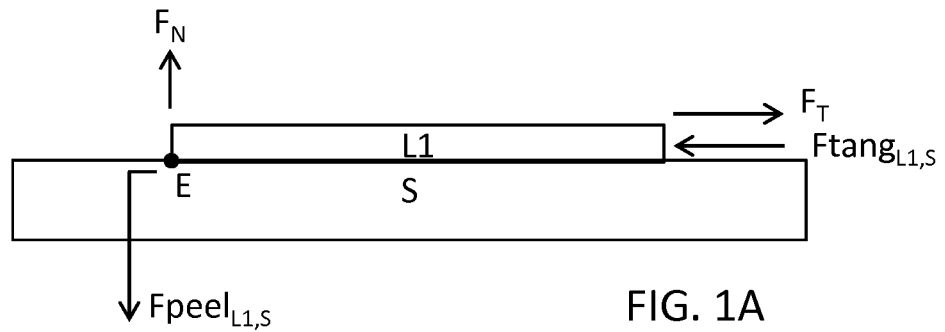
FIG. 1 illustrates three exemplary layer structures (A, B, C) that exemplify some of the principles exploited in the present invention.

FIG. 1 illustrates three exemplary layer structures (A, B, C) that exemplify some of the principles exploited in the present invention. In FIG. 1A, layer L1 is attached to a substrate S, for example by van der Waals forces, or an adhesive layer. Substrate S and layer L1 are planar layers that extend in a direction normal to the paper. In order to separate layer L1 from substrate S, a force $F_N$ can be applied in a direction normal to the surface of substrate S at edge E of layer L1 as indicated. Separation of layer L1 occurs when a peel retaining force $Fpeel_{L1,S}$ is overcome. Alternatively a force $F_T$ can be applied in a direction that is tangential to the surface of substrate S to remove layer L1. Separation of layer L1 occurs when a tangential retaining force $Ftang_{L1,S}$ is overcome. Conventionally $Fpeel_{L1,S}$ is much less than $Ftang_{L1,S}$ due to the reduced surface area of the peeling zone around edge E as compared to the interface area between layer L1 and substrate S.

Figure 1B:
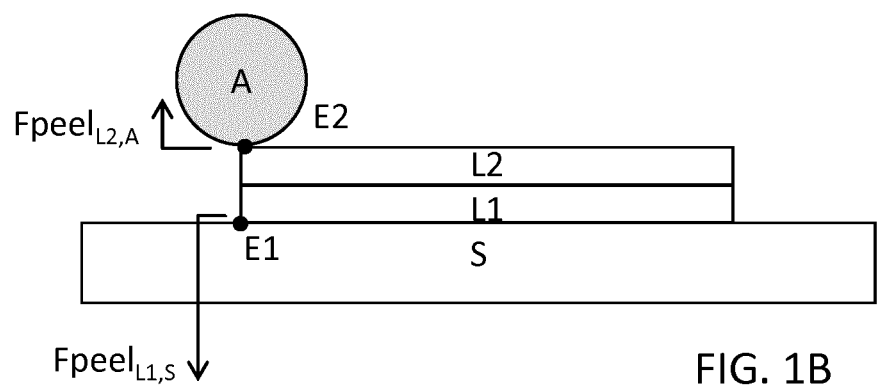

In FIG. 1B, additional layer L2 is attached to layer L1. Layer L2 may represent an adhesive layer via which layer L1 can be attached to the surface of an article A. The adhesive layer may for example be a pressure-sensitive adhesive. The adhesive layer may also optionally be coated by a protective layer, referred to as a removable outer liner layer, commonly termed a "liner" which is used to protect the adhesive layer during assembly of the stack S-L1-L2. The surface of article A may for example be formed from a metal, or a polymer. In order to transfer layer L1 to an article A, layer L1 must be released from substrate S. In the case of the exemplary circular cross section article shown this may be achieved by removing the optional liner removable outer liner layer and rolling article A across the surface of layer L2. Articles with this and other shapes may be so attached by pressing the article into layer L2. Again, $Fpeel_{L1,S}$ defines a peel retaining force that must be overcome by applying a force in a direction normal to the surface of substrate S at edge E1 in order to release layer L1 from substrate S. Likewise $Fpeel_{L2,A}$ defines a peel retaining force that must be overcome by applying a force in a direction normal to the surface of article A at edge E2 in order to release layer L2 from article A. In order to attach article A to layer L1 via L2 and to subsequently release substrate S, $Fpeel_{L2,A}$ should be greater than $Fpeel_{L1,S}$. The ratio $Fpeel_{L2,A}$:$Fpeel_{L1,S}$ should preferably be greater than or equal to 2:1, but is preferably greater than or equal to 10:1, 100:1 or 1000:1. A high ratio is preferred because it allows thinner materials to be used, and higher transfer yield to be achieved. Consequently by pressing and pulling apart article A and substrate S, or by rolling article A across the surface of layer L2, layer L1 may be attached to article A and layer L1 is released from substrate S.

A limitation of the arrangement in FIG. 1B is that the need to make the peel retaining force $Fpeel_{1,S}$ as small as possible in order to permit ease of release of layer L1, results in making the stack S-L1-L2, vulnerable to the spontaneous peeling of layer L1 during assembly of the stack. When the optional liner layer is used, removal of the liner layer from the surface of L2 also risks causing de-lamination of layer L1. Moreover, accurate alignment is required between layers L1 and L2 in order to prevent excess adhesive from spilling onto substrate S.

Figure 1C:
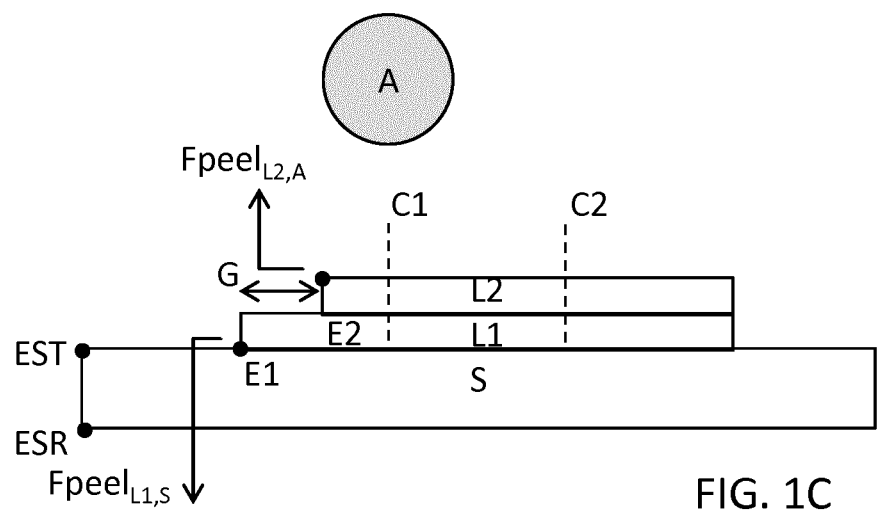

The arrangement in FIG. 1C resolves the limitations of the FIG. 1B arrangement by staggering the edges E1, E2, of layer 1, and layer 2 respectively. Layer L2 is within the extent of layer L1 such that there is a gap G between the edge E2 of adhesive layer L2 and the edge E1 of layer L1. Consequently, although L1 is relatively weakly attached to substrate S, a force applied at edge E2 in a normal direction with respect to the interface between L1 and S, must overcome not just the peel retaining force $Fpeel_{L1,S}$ but a shear, or tangential retaining force as described in relation to $Ftang_{1,S}$ of FIG. 1A. By thus reducing the risk of de-lamination of foil L2 at edge E2, the robustness of the stack of layers S-L1-L2 is improved. This allows same degree of manipulation of the object A on the surface of adhesive layer L2 during its attachment to L2, without causing de-lamination. When an optional removable outer liner layer is used on the surface of L2 the risk of de-lamination during removal of the liner is also reduced. Moreover, by removing the need to accurately align the adhesive layer L2 and layer L1, manufacturing is simplified.

The principles illustrated in FIGS. 1B and 1C can be further extended by wrapping at least layer L1, which is relatively weakly-attached to substrate S, beyond edge EST that faces layer L2. Layer L1 may further include a transducer that it is desirable to attach to object A. This further reduces the risk of de-lamination. Furthermore it increases the amount of usable surface area of substrate S, thereby reducing wastage. By wrapping layer L1 even further, to beyond edge ESR that lies on the opposite face of substrate S, the risk of de-lamination is even further reduced. FIG. 1C also illustrates exemplary cut positions C1, C2 at which layer L1 may be cut in a normal direction respective the surface of substrate S, in order to define a perimeter of a section of layer L1 that it is desirable to selectively attach to article A. By providing such cut lines along the perimeter, when article A is pressed into or rolled across the exposed surface of layer L2 the force that is required to remove the portion of layer L2 within the perimeter defined by the cut lines is reduced. When the cut lines define a continuous path, the force that is required to remove the portion of layer L2 within the perimeter is reduced to the peel retaining force $Fpeel_{L1,S}$. Partial, or discontinuous cut lines along the perimeter may also be used to reduce the force that is required to remove the portion of layer L2 within the perimeter towards the peel retaining force $Fpeel_{L1,S}$.

Figure 2A:
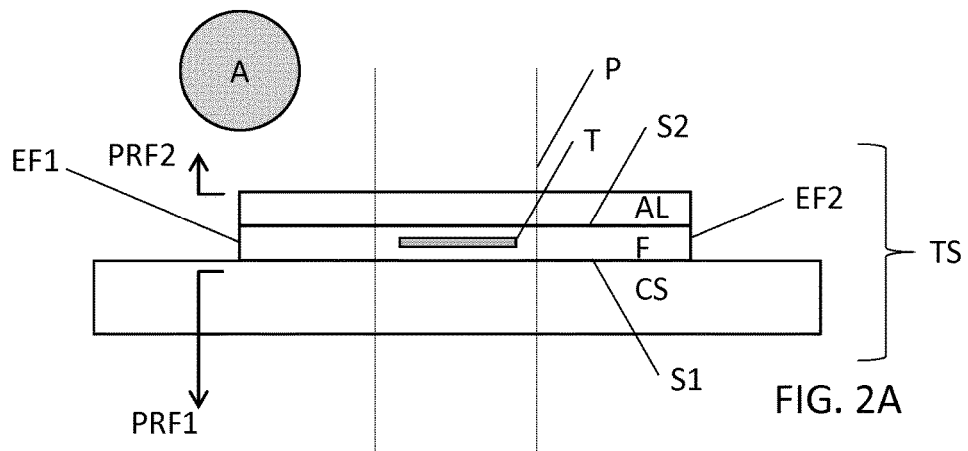
FIG. 2 illustrates an embodiment in cross section (FIG. 2A) plan (FIG. 2B) and perspective (FIG. 2C) views of a transfer stack TS in accordance with some aspects of the invention.
Figure 2B:
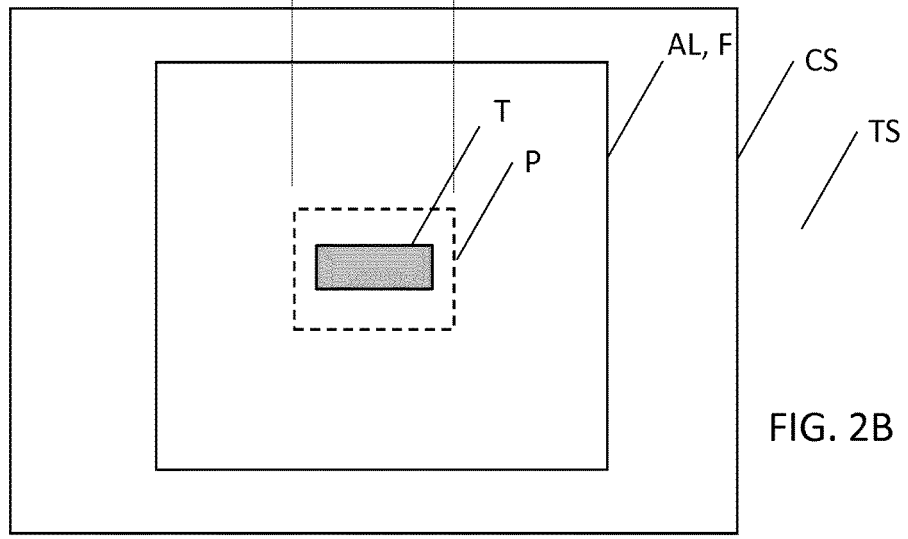
Figure 2C:
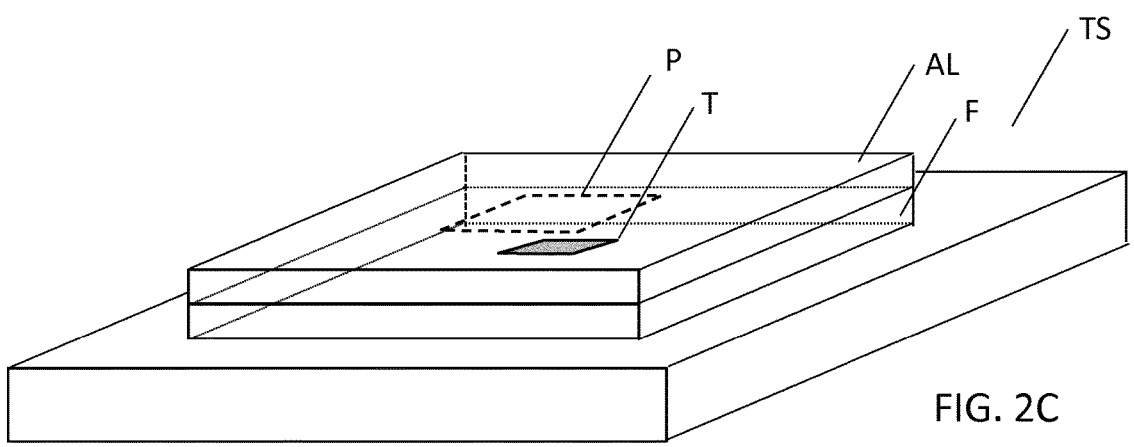

FIG. 2 illustrates an embodiment in cross section (FIG. 2A) plan (FIG. 2B) and perspective (FIG. 2C) views of a transfer stack TS in accordance with some aspects of the invention. The transfer stack of FIG. 2 is adapted for transferring a portion of a foil within a perimeter P that includes a transducer T to an article A.

Preferably the article A is a medical device such as a medical needle. Alternatively the article may be a support device in general on which the transducer T is ultimately used. The surface of article A may for example be formed from a metal, including stainless steel, steel, aluminium, copper, chrome; or a polymer, including synthetic rubber, phenol formaldehyde resin (or Bakelite), neoprene, nylon, polyvinyl chloride (PVC or vinyl), polystyrene, polyethylene, polypropylene, polyacrylonitrile, PVB, silicone, but is not limited to these example materials. Transfer stack TS includes carrier substrate CS; foil F comprising transducer T that is laterally surrounded by a perimeter P, the perimeter P being within the lateral extent of the foil F; and an adhesive layer AL. Carrier substrate CS may for example be formed from materials such as silicone, rubber, PVC, polyethylene, PolyTetraFluoroEthylene, wax, or a thermoplastic fluoropolymer such as Polyvinylidene fluoride. Such materials exhibit a degree of malleability that can benefit the process of assembling the transfer stack as described later. Preferably carrier substrate CS is formed from silicone. Alternatively more rigid materials such as Perspex or glass may be used for the carrier substrate, e.g. when layer L1 is attached to substrate S via a second adhesive layer. However, when layer L1 is attached to substrate S via van der Waals forces the more malleable materials listed exemplified above are preferred since they provide more deformation, and this enhances the van der Waals force interactions. Foil F may for example be formed from polymer materials, including Polyethylene terephthalate (PET), Polyimides (PI), Polyamides (PA). In one example, transducer T is formed within foil F, for example using a molding process, and in another example the transducer T is laminated between two or more polymer sheets that are bonded together to form single foil F having outermost surfaces S1, S2. Electrical wires or electrical conductive strips that make electrical contact with transducer T may also be included within foil F. Transducer T may be any transducer, i.e. a device that converts electrical energy to another form of energy, or vice-versa. Non-limiting specific sensor examples include an ultrasound transducer, a temperature sensor, a photosensor, a vibration sensor, an acoustic sensor a MEMs sensor, a pressure sensor; and non-limiting actuator examples include an ultrasound emitter, an acoustic emission device, a piezoelectric vibrator, a heater, and a light-generating device such as an LED or OLED. Preferably transducer T is formed from a Polyvinylidene fluoride, i.e. PVDF, layer, or a PVDF co-polymer such as polyvinylidene fluoride trifluoroethylene (P(VDF-TrFE)) layer or a PVDF ter-polymer such as P(VDF-TrFE-CTFE), and is an ultrasound transducer. The PVDF layer may be laminated between the pressure sensitive adhesive, i.e. PSA coated surfaces of two PET sheets to form a single foil F. Pressure sensitive adhesives form a class of materials that form an adhesive bond upon application of pressure. Suitable pressure sensitive adhesives include product 2811CL made by the 3M corporation. These may be supplied as PSA-coated polymer sheets such as product 9019 supplied by the 3M corporation. Perimeter P defines an outline around transducer T on the foil's surface and may coincide with the lateral extent of the transducer, or may additionally include a margin around the transducer, the latter situation being illustrated in FIG. 2B.

In the embodiment of FIG. 2, first surface S1 of foil F is attached to the carrier substrate, and the adhesive layer AL is attached to second surface S2 of foil F. Preferably first surface S1 of foil F is attached to carrier substrate CS by means of a van der Waals force. Van der Waals forces are intermolecular forces that include Keesom forces, Debye forces, and London dispersion forces. Attachment of first surface S1 of foil F is to carrier substrate CS via Van der Waals forces is preferred since this provides a relatively weak bond strength between the first surface of the foil and the carrier substrate. As described above, this may be used to provide temporary attachment of foil F, in preparation for its subsequent release from carrier substrate CS. Alternatively a second adhesive layer AL2, not illustrated, such as a pressure sensitive adhesive layer as described above may be disposed between foil F and carrier substrate CS to achieve the desired temporary attachment. Furthermore, adhesive layer AL is attached to second surface S2 of foil F. Preferably the second surface of the foil is provided by a surface of a PSA-coated sheet.

In the embodiment of FIG. 2, first surface S1 of foil F is separable from carrier substrate CS by applying in a direction normal to the carrier substrate CS and at an edge EF1, EF2 of foil F a peeling force that overcomes a first peel retaining force PRF1. Furthermore, adhesive layer AL is configured to provide adhesion between foil F and article A such that when article A is attached to foil F via adhesive layer AL, second surface S2 of foil F is separable from the surface of the article A by applying in a direction normal to the surface of article A and at edge EF1, EF2 of foil F a peeling force that overcomes a second peel retaining force PRF2. Adhesive layer AL may be an adhesive layer in general. Moreover, second peel retaining force PRF2 is greater than first peel retaining force PRF1. Preferably adhesive layer AL is formed from pressure-sensitive adhesive, i.e. PSA, which provides a reliable bond of the desired strength; thus, a retaining force that is greater than the retaining force provided by the preferred van der Waals forces that preferably provide first peel retaining force PRF1.

In the embodiment of FIG. 2, foil F is cut along at least a portion of perimeter P that includes the transducer T such that when article A is attached to the foil and is subsequently peeled in a direction normal to carrier substrate CS the portion of the foil within perimeter P becomes separated from the carrier substrate at the perimeter P by overcoming the first peel retaining force PRF1 and the portion of the foil within the perimeter P remains attached to the article. In so doing, transducer T including the portion of foil inside perimeter P is selectively and reliably attached to article A.

In another embodiment of the invention not illustrated, the embodiment of FIG. 2 is further provided with a removable outer liner layer ROL. The removable outer liner layer ROL acts to protect the adhesive layer during assembly of the transfer stack, and prior to its attachment to an article. The removable outer liner may be formed, for example, from a waxed paper sheet which allows it to be easily removable from adhesive layer AL prior to attaching article A to the adhesive layer.

Figures 3A, 3B:
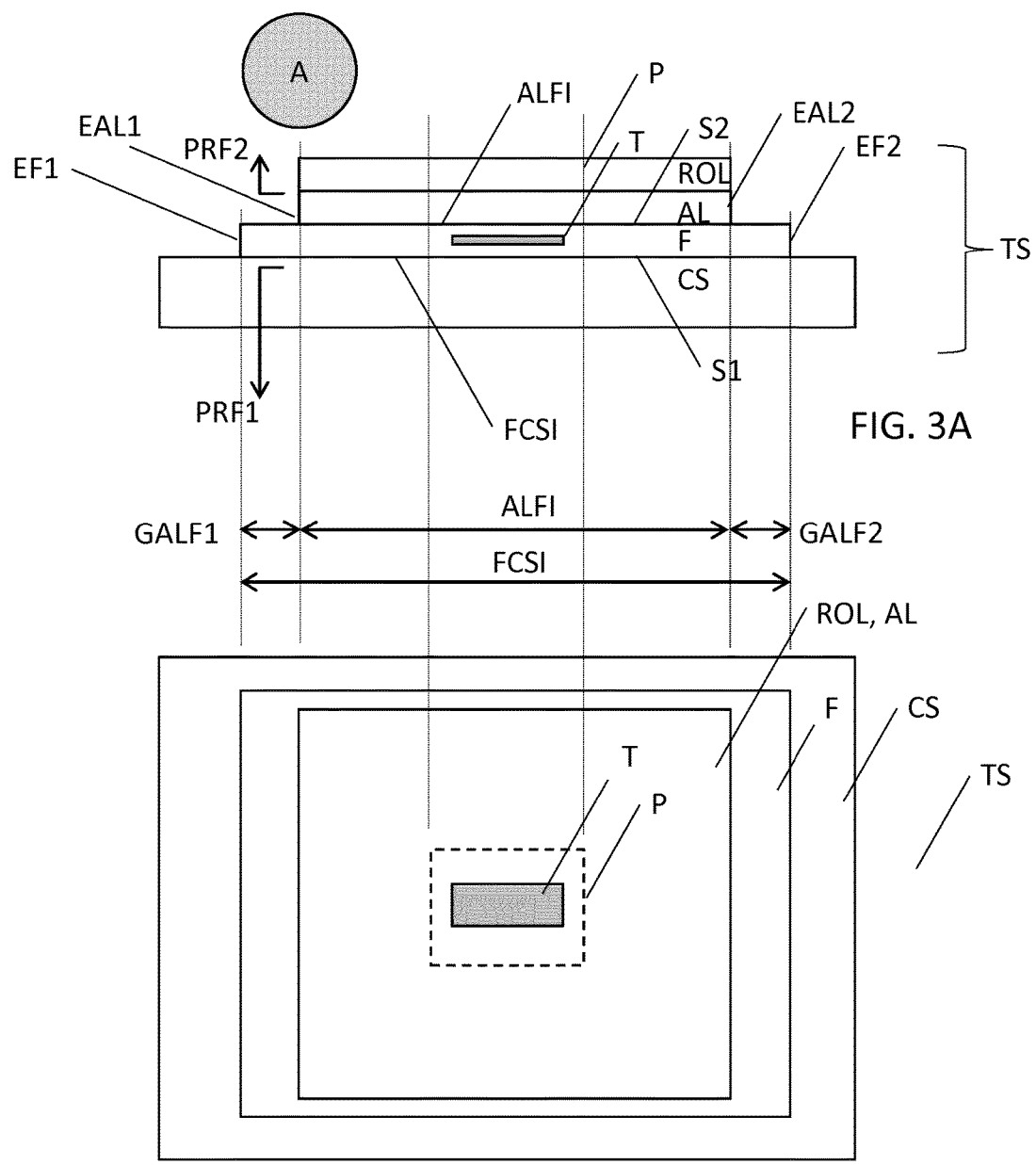
FIG. 3 illustrates another embodiment in cross section (FIG. 3A) and plan (FIG. 3B) views of a transfer stack TS in accordance with some aspects of the invention

FIG. 3 illustrates another embodiment in cross section (FIG. 3A) and plan (FIG. 3B) views of a transfer stack TS in accordance with some aspects of the invention. The embodiment of FIG. 3, differs from that of FIG. 2 in that it further includes optional removable outer liner layer ROL whose properties are described above. The embodiment of FIG. 3 may also be used without the ROL layer. The embodiment of FIG. 3, further differs from that of FIG. 2 in that the interface between adhesive layer AL and foil F defines an adhesive layer-foil interface ALFI, and in that the interface between foil F and carrier substrate CS defines a foil-carrier substrate interface FCSI. Moreover the extent of adhesive layer-foil interface ALFI extends beyond perimeter P; and the extent of the adhesive layer-foil interface ALFI is within the extent of the foil-carrier substrate interface FCSI such that there are gaps GALF1, GALF2 between the edges EAL1, EAL2 of the adhesive layer AL and the edges of the foil EF1, EF2. These gaps may be present in one i.e. x direction or two perpendicular i.e. x and y directions.

The gaps GALF1, GALF2 improve the resistance of the foil to peeling at foil edges EF1, EF2 during assembly of the transfer stack, for example when applying adhesive layer AL to the foil F. This is in part because the deposition of adhesive layer AL is performed away from foil edges EF1, EF2 which are particularly susceptible to delamination as a consequence of forces applied normally with respect to the carrier substrate. Also, when optional removable liner ROL is removed in order to attach the transducer within perimeter P to article A there is less tendency for the foil to delaminate from carrier substrate CS. This is achieved because in order to separate the foil from the carrier substrate at the adhesive layer edges EAL1, EAL2, a normally-applied peeling force at these edges EAL1, EAL2 must overcome a tangential retaining force between the foil and the carrier substrate at this position, and the tangential retaining force is conventionally much greater than the, normally defined, first peel retaining force PRF1. This can be visualized as the difference between peeling a section of sticky tape from a surface. This principle is described above with respect to FIG. 1C in particular. When a normally-applied force is used, removal is relatively easy. When a shear, or tangential force is applied, it is much harder to remove the layer. The gaps at the adhesive layer edges EAL1, EAL2 resolve a normally-applied force at the adhesive layer to an in-plane force at the edges of the foil. The improved resistance to peeling also increases the stability of the transfer stack during subsequent handling. Consequently a transfer stack is provided that has both a relatively weak attachment between the foil and the carrier substrate, this being desired for ease of subsequent release transducer within perimeter P during its attachment to article A, and a relatively stronger adhesive layer AL that provides good bonding to the article.

The length of the gaps GALF1, GALF2 described above is preferably greater than or equal to 1 mm, or greater than or equal to 5 mm, or 10 mm to achieve the above benefits in terms of robustness during handling and assembly.

In another embodiment of the invention the transfer stack is further provided with a support substrate SS. Such may be used in combination with any of the embodiments described herein, particularly the embodiments of FIG. 2 and FIG. 3. The support substrate SS is attached to the carrier substrate CS and is formed from a material having an indentation hardness value that exceeds the indentation hardness value of the carrier substrate CS. The increased indentation hardness provided by the support substrate as compared to that of the carrier substrate facilitates improved bonding, specifically improved uniformity of bonding, between the foil and the carrier substrate during assembly of the transfer stack, for example during assembly of the transfer stack when the foil is pressed against the carrier substrate. This benefit occurs in particular when van der Waals forces are used to attach a polyimide foil to a silicone carrier substrate.

Figure 4A:
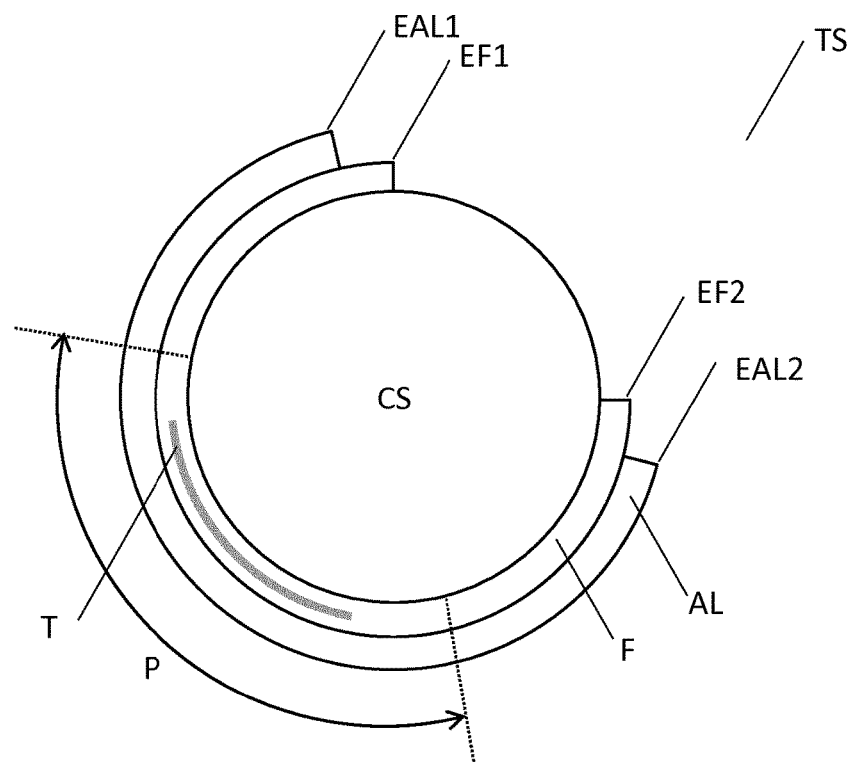
FIG. 4 illustrates in cross section (FIG. 4A) and in perspective (FIG. 4B) views a transfer stack TS in which the carrier substrate CS is in the form of a roller.
Figure 4B:
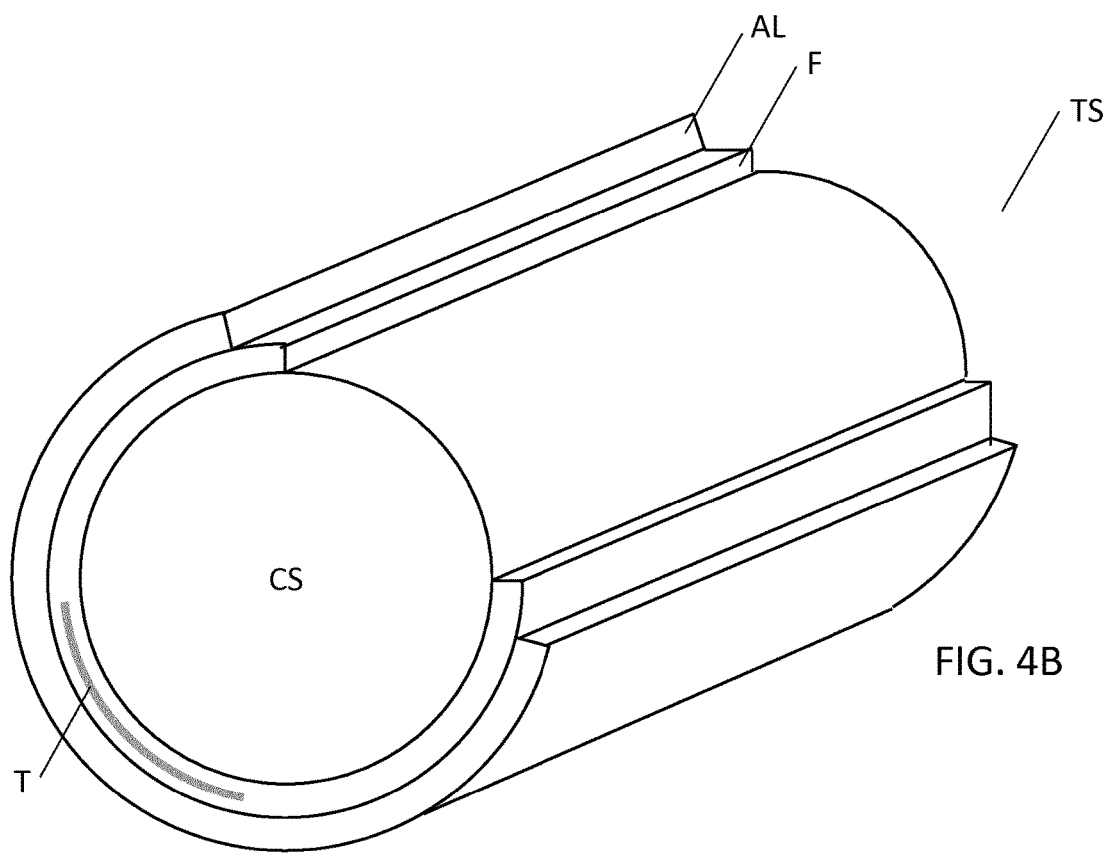

In some embodiments of the invention support substrate SS is formed from a curved surface, such as a roller. Moreover and the transfer stack (TS) is wrapped around the roller. A curved surface, or roller is particularly useful in rapidly transferring the portion of the foil within perimeter P to an article having a planar surface. FIG. 4 illustrates in cross section (FIG. 4A) and in perspective (FIG. 4B) views a transfer stack TS in which the carrier substrate CS is in the form of a roller.

Figure 5A:
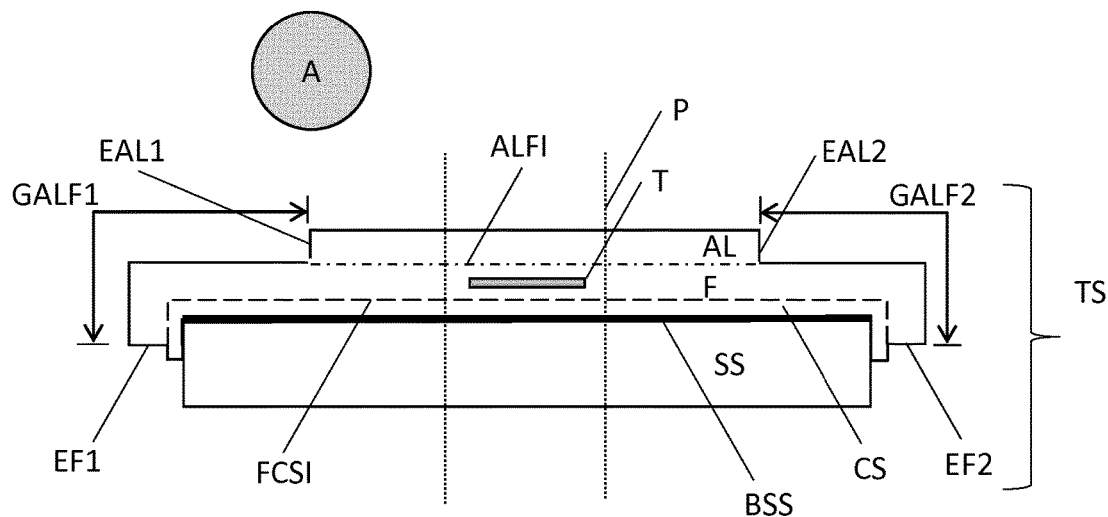
FIG. 5 illustrates in cross section two embodiments of a transfer stack TS in which the support substrate SS has a planar surface with a boundary BSS that contacts the foil F; and in which the carrier substrate CS is in the form of a layer; and in which the foil-carrier substrate interface FCSI extends beyond the boundary of the planar surface of the support substrate BSS.
Figure 5B:
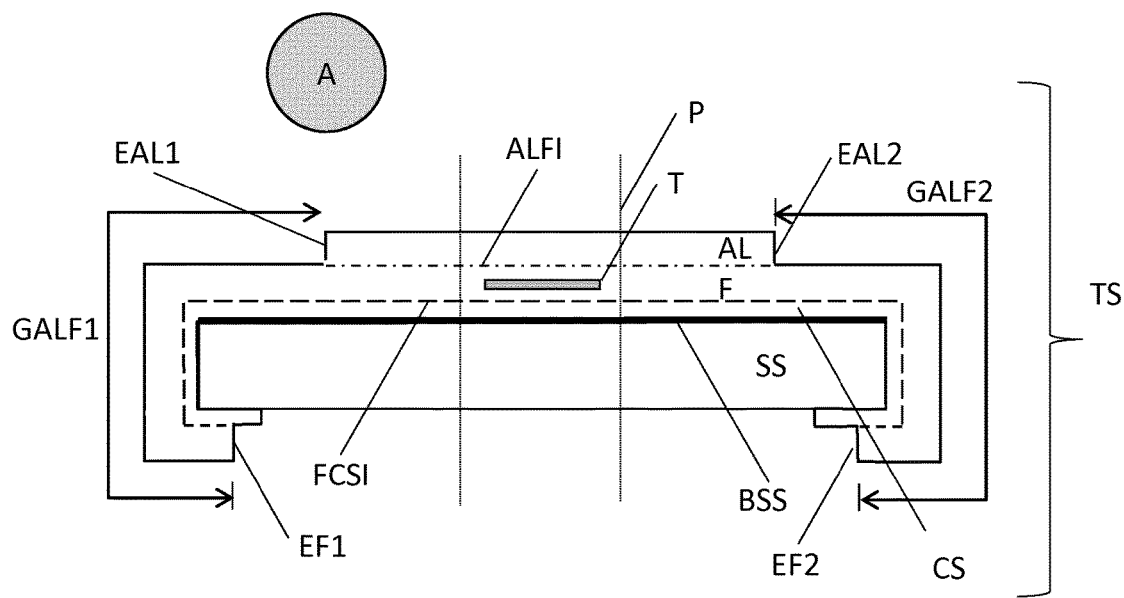

In other embodiments support substrate SS may be a planar layer. FIG. 5 illustrates in cross section two embodiments of a transfer stack TS in which the support substrate SS has a planar surface with a boundary BSS that contacts the foil F; and in which the carrier substrate CS is in the form of a layer; and in which the foil-carrier substrate interface FCSI extends beyond the boundary of the planar surface of the support substrate BSS. In FIG. 5A the foil-carrier substrate interface FCSI extends to a position between the support substrate SS edges that define the boundary and the support substrate SS edges of an opposing surface of the support substrate that faces away from the transducer, and in FIG. 5B the foil-carrier substrate interface FCSI extends beyond the support substrate SS edges of an opposing surface of the support substrate that faces away from the transducer. By so arranging the foil-carrier substrate interface FCSI, improved resistance to peeling in a direction normally to the support substrate is achieved because in order to peel the foil from the carrier substrate a tangential retaining force at the boundary BSS of the planar surface of the support substrate must be overcome. Even higher resistance to peeling is achieved as illustrated in FIG. 5B when the foil extends to the opposite side of the support substrate SS that faces away from the transducer.

Figure 6A:
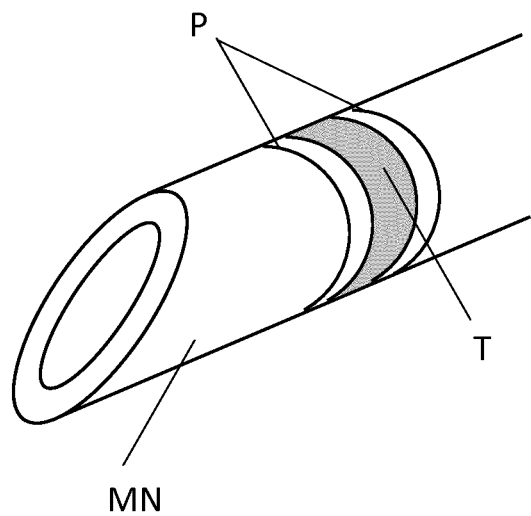
FIG. 6 illustrates another embodiment in which a portion of the foil F within perimeter P is attached to a medical needle MN, as an assembled device in FIG. 6A, in FIG. 6B by rolling the needle MN across the surface of the adhesive layer AL, and in FIG. 6C by pressing the needle MN into the adhesive layer.
Figure 6B:
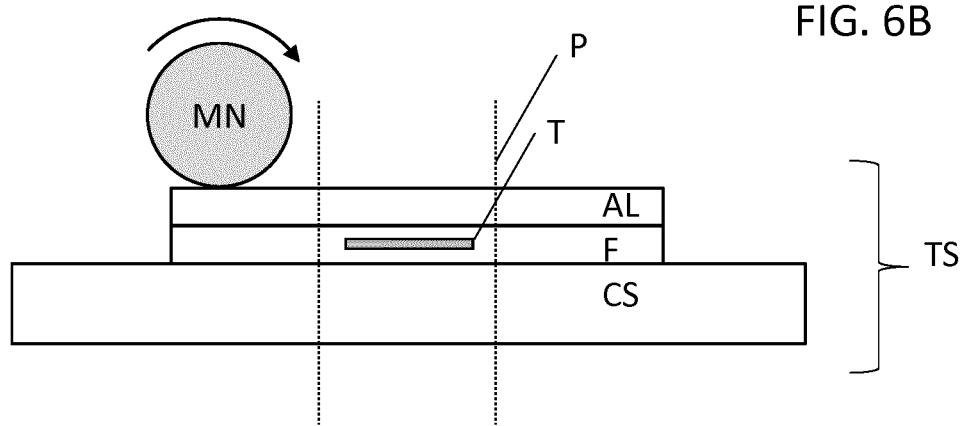
Figure 6C:
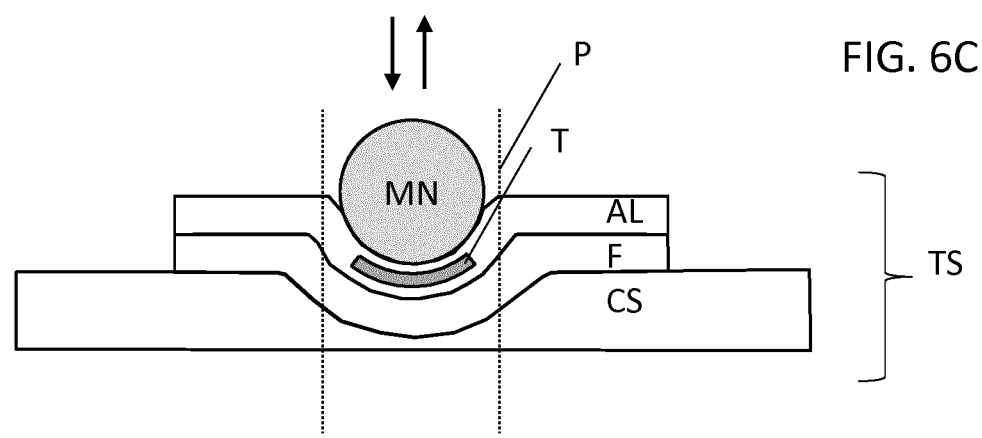

FIG. 6 illustrates another embodiment in which a portion of the foil F within perimeter P is attached to a medical needle MN, as an assembled device in FIG. 6A, in FIG. 6B by rolling the needle MN across the surface of the adhesive layer AL, and in FIG. 6C by pressing the needle MN into the adhesive layer. Instead of a medical needle item MN may alternatively be a different medical device, such as a catheter or a cannula or the like, or indeed any type of support structure to which transducer T can be transferred. As shown in FIG. 6A, adhesive layer AL secures foil F that includes transducer T to medical needle MN. The cut along at least a portion of the perimeter P ensures that after rolling the needle along the carrier substrate, or separating the needle and the carrier substrate, the portion of foil within perimeter P remains attached to the medical needle by virtue of the greater bond strength between the adhesive layer and the medical needle, as compared to that between the foil and the carrier substrate CS. The cut along the perimeter may be continuous or alternatively comprise a series of discrete cuts into foil F in the form of a perforated line.

Figure 7A:
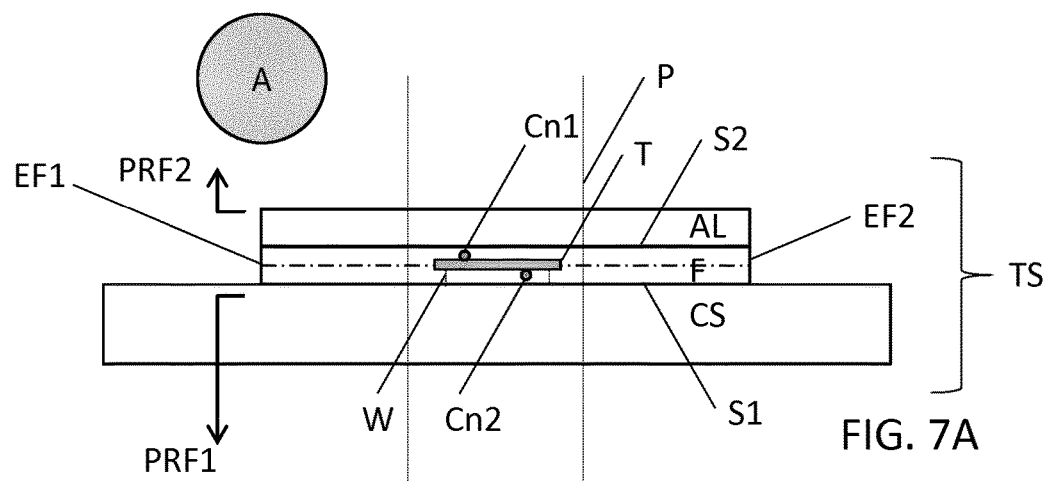
FIG. 7 illustrates an embodiment in cross section (FIG. 7A) and plan (FIG. 7B) views of a transfer stack TS in accordance with some aspects of the invention.
Figure 7B:
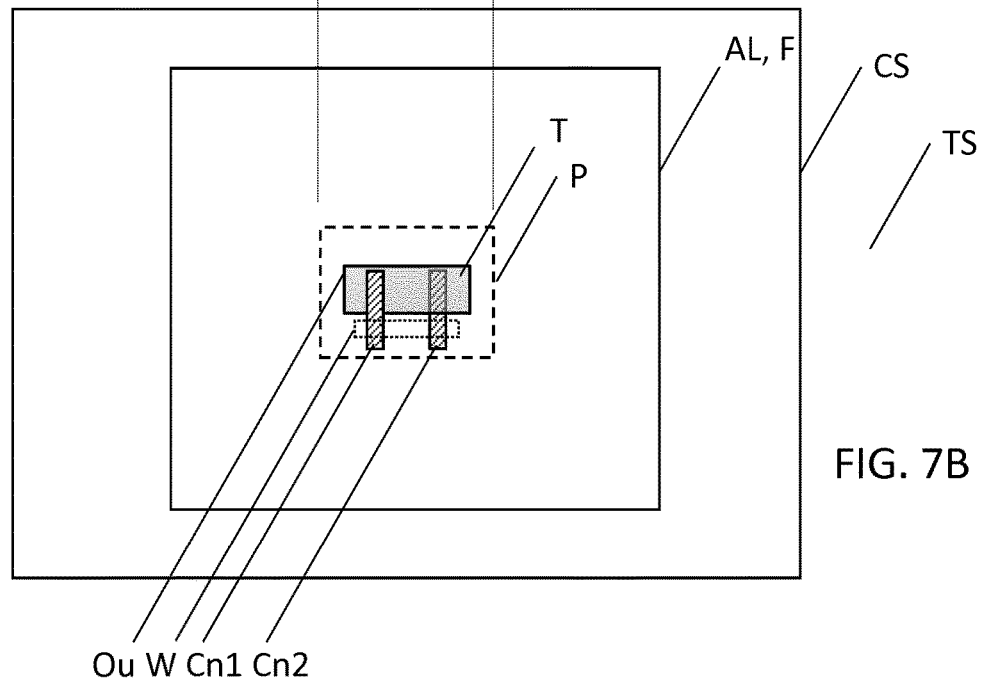

FIG. 7 illustrates an embodiment in cross section (FIG. 7A) and plan (FIG. 7B) views of a transfer stack TS in accordance with some aspects of the invention. The items in FIG. 7 correspond to those in FIG. 2. Additionally, in transfer stack TS illustrated in FIG. 7, foil F comprises two sheets between which transducer T is laminated. The outer surfaces of the two laminated sheets in FIG. 7 provide the first surface S1 and the second surface S2 of foil F. The two sheets are preferably formed from polymers, preferably electrical insulating polymers, although one of the sheets may alternatively be made from an electrical conductor. When polymer sheets are used this encapsulation of transducer T hermetically seals transducer T, preventing it from interacting with the environment. A conductive sheet may be used to electrically screen transducer T or to electrically screen electrical conductors attached thereto. Moreover, transducer T in transfer stack TS illustrated in FIG. 7 is provided by a planar layer having a first surface and a second surface that are both parallel to the planar layer. The planar layer is arranged parallel to both the first surface S1 and the second surface S2 of foil F. Transducer T further comprises first electrical conductor Cn1 that is in electrical contact with the first surface of transducer T and second electrical conductor Cn2 that is in electrical contact with the second surface of the transducer T. Electrical conductors Cn1, Cn2 may for example be electrical wires, or conductive tracks or traces formed from electrical conductors such as metals. Wires with a circular cross section are preferred owing to their high flexibility. Moreover, transducer T has an outline Ou that is within perimeter P. Transducer T may be one of the transducers described elsewhere herein, such as an ultrasound transducer. Moreover, the first electrical conductor Cn1 and the second electrical conductor Cn2 both extend beyond the outline Ou in the same direction and are separated laterally with respect to the planar layer of the transducer T such that the first electrical conductor Cn1 and the second electrical conductor Cn2 do not overlap in a direction perpendicular to the planar layer of the transducer T. The lateral separation reduces the total thickness of the transfer stack, reduces the capacitance between electrical conductors Cn1 and Cn2, and improves their electrical isolation. Moreover, at least a portion of one of the two polymer sheets includes a window W in a portion of the foil between the outline Ou and the perimeter P for making electrical contact with the first electrical conductor Cn1 and with the second electrical conductor Cn2. Advantageously this arrangement in which conductors Cn1 and Cn2 are both laminated between the two sheets of foil F within the portion of the foil between the outline Ou and the perimeter P, provides a simplified means for making electrical contact to electrical conductors Cn1 and Cn2 because only material from one of the two sheets needs to be removed; and at the same time provides electrical contact with both sides of transducer T. Preferably, as in the illustration, the sheet facing carrier substrate CS, includes window W in order to make electrical contact with electrical conductors Cn1 and Cn2 when the portion of foil F within perimeter P is attached to article A. Likewise the other sheet may include window W.

In all the embodiments described herein, typical thickness dimensions of the various layers are as follows: support substrate 1-10 millimeters (or a roller diameter of 10-100 millimeters); carrier substrate 50-500 microns; foil 1-50 microns; adhesive layer 5-50 microns; removable outer layer 4-35 microns; however it should be appreciated that these dimensions are purely illustrative and the invention is not limited to these examples.

To summarize, a transfer stack for transferring, to an article, a portion of a foil comprising a transducer, is disclosed herein.

Whilst the invention has been illustrated and described in detail in the drawings and foregoing description in relation to a medical needle, such illustrations and description are to be considered illustrative or exemplary and not restrictive; the invention is not limited to the disclosed embodiments and can be used for transferring transducers to articles in general.

The invention claimed is:

1. A transfer stack for transferring a portion of a foil within a perimeter that includes a transducer to an article such as a medical device or a medical needle; the transfer stack comprising:
    a carrier substrate;
    a foil comprising a transducer that is laterally surrounded by a perimeter, the perimeter being within the lateral extent of the foil; and
    an adhesive layer;
    wherein a first surface of the foil is attached to the carrier substrate, and the adhesive layer is attached to the second surface of the foil;
    wherein the first surface of the foil is separable from the carrier substrate by applying in a direction normal to the carrier substrate and at an edge of the foil a peeling force that overcomes a first peel retaining force;
    wherein the adhesive layer is configured to provide adhesion between the foil and an article such that when the article is attached to the foil via the adhesive layer the second surface of the foil is separable from the surface of the article by applying in a direction normal to the surface of the article and at the edge of the foil a peeling force that overcomes a second peel retaining force; and
    wherein the second peel retaining force is greater than the first peel retaining force; and
    wherein the foil is cut along at least a portion of the perimeter that includes the transducer such that when the article is attached to the foil via the adhesive layer and subsequently peeled in a direction normal to the carrier substrate the portion of the foil within the perimeter becomes separated from the carrier substrate at the perimeter by overcoming the first peel retaining force and the portion of the foil within the perimeter (P) remains attached to the article.

2. The transfer stack according to claim 1, wherein the first surface of the foil is attached to the carrier substrate by means of at least one of i) a van der Waals force, ii) a second adhesive layer such as a pressure sensitive adhesive layer.

3. The transfer stack according to claim 1, wherein the adhesive layer is formed from a pressure sensitive adhesive.

4. The transfer stack according to claim 1, wherein the carrier substrate is formed from a malleable material; for example silicone, PolyTetraFluoroEthylene, rubber, wax, a thermoplastic fluoropolymer such as Polyvinylidene fluoride.

5. The transfer stack according to claim 1, wherein the adhesive layer further comprises a removable outer liner layer.

6. The transfer stack according to claim 1, wherein said transfer stack further comprises a support substrate;
    wherein the support substrate is attached to the carrier substrate; and
    wherein the support substrate is formed from a material having an indentation hardness value that exceeds the indentation hardness value of the carrier substrate.

7. The transfer stack according to claim 6, wherein the support substrate is in the form of a roller and the transfer stack is wrapped around the roller.

8. The transfer stack according to claim 6, wherein the interface between the adhesive layer and the foil defines an adhesive layer-foil interface; and wherein the interface between the foil and the carrier substrate defines a foil-carrier substrate interface; and wherein the extent of the adhesive layer-foil interface extends beyond the perimeter; and wherein the extent of the adhesive layer-foil interface is within the extent of the foil-carrier substrate interface such that there are gaps between the edges of the adhesive layer and the edges of the foil; and wherein the support substrate has a planar surface with a boundary that contacts the foil; and
    wherein the carrier substrate is in the form of a layer;
    and wherein the foil-carrier substrate interface extends beyond the boundary of the planar surface of the support substrate.

9. The transfer stack according to claim 8, wherein the planar surface of the support substrate faces the adhesive layer.

10. The transfer stack according to claim 1, wherein the interface between the adhesive layer and the foil defines an adhesive layer-foil interface, and wherein the interface between the foil and the carrier substrate defines a foil-carrier substrate interface; and wherein the extent of the adhesive layer-foil interface extends beyond the perimeter;

and wherein the extent of the adhesive layer-foil interface is within the extent of the foil-carrier substrate interface such that there are gaps between the edges of the adhesive layer and the edges of the foil.

11. The transfer stack according to claim 7, wherein the gaps are each greater than or equal to 1 mm.

12. The transfer stack according to claim 10, wherein the transducer is an ultrasound transducer.

13. The transfer stack according to claim 1, wherein the foil comprises two polymer sheets between which the transducer is laminated; and wherein the outer surfaces of the two laminated sheets provide the first surface and the second surface of the foil.

14. The transfer stack according to claim 13, wherein the transducer is provided by a planar layer having a first surface and a second surface that are both parallel to the planar layer, the planar layer being arranged parallel to both the first surface and the second surface of the foil, and wherein the transducer further comprises a first electrical conductor configured to make electrical contact with the first surface of the transducer and a second electrical conductor configured to make electrical contact with the second surface of the transducer; and wherein the transducer has an outline that is within the perimeter; and wherein the first electrical conductor and the second electrical conductor both extend beyond the outline in the same direction and are separated laterally with respect to the planar layer of the transducer such that the first electrical conductor and the second electrical conductor do not overlap in a direction perpendicular to the planar layer of the transducer; and wherein at least a portion of one of the two polymer sheets includes a window in a portion of the foil between the outline and the perimeter for making electrical contact with the first electrical conductor and with the second electrical conductor.

15. Article, for example a medical device or a medical needle, comprising the portion of the foil within the perimeter of claim 1.

16. A method of forming a transfer stack for transferring a portion of a foil within a perimeter that includes a transducer to an article such as a medical device or a medical needle; the method comprising the steps of:

providing a carrier substrate;

providing a foil comprising a transducer that is laterally surrounded by a perimeter, the perimeter being within the lateral extent of the foil; and providing an adhesive layer;

attaching a first surface of the foil to the carrier substrate;

attaching the adhesive layer to the second surface of the foil;

wherein the first surface of the foil is separable from the carrier substrate by applying in a direction normal to the carrier substrate and at an edge of the foil a peeling force that overcomes a first peel retaining force; and wherein the adhesive layer is configured to provide adhesion between the foil and an article such that when the article is attached to the foil via the adhesive layer the second surface of the foil is separable from the surface of the article by in a direction normal to the surface of the article and at the edge of the foil a peeling force that overcomes a second peel retaining force; and wherein the second peel retaining force is greater than the first peel retaining force; and cutting the foil along at least a portion of the perimeter that includes the transducer, such that when the article is attached to the foil via the adhesive layer and subsequently peeled in a direction normal to the carrier substrate the portion of the foil within the perimeter becomes separated from the carrier substrate at the perimeter by overcoming the first peel retaining force and the portion of the foil within the perimeter remains attached to the article.

17. The method according to claim 16, wherein said method further comprises the steps of:

providing a support substrate wherein the support substrate is formed from a material having an indentation hardness value that exceeds the indentation hardness value of the carrier substrate; and attaching the support substrate to the carrier substrate.

18. The method according to claim 17, wherein the adhesive layer further comprises a removable outer liner layer, and wherein the interface between the adhesive layer and the foil defines an adhesive layer-foil interface; and wherein the interface between the foil and the carrier substrate defines a foil-carrier substrate interface; and wherein the extent of the adhesive layer-foil interface extends beyond the perimeter; and wherein the extent of the adhesive layer-foil interface is within the extent of the foil-carrier substrate interface such that there are gaps between the edges of the adhesive layer and the edges of the foil and wherein the support substrate has a planar surface with a boundary that contacts the foil; and wherein the carrier substrate is in the form of a layer;

and wherein the foil-carrier substrate interface extends beyond the boundary of the planar surface of the support substrate.

19. The method according to claim 18, wherein the planar surface of the support substrate faces the adhesive layer.

20. The method according to claim 16, wherein the transducer is an ultrasound transducer.

21. The method according to claim 16, wherein the foil comprises two polymer sheets between which the transducer is laminated; and wherein the outer surfaces of the two laminated sheets provide the first surface and the second surface of the foil.

22. The method according to claim 21, wherein the transducer is provided by a planar layer having a first surface and a second surface that are both parallel to the planar layer, the planar layer being arranged parallel to both the first surface and the second surface of the foil, and wherein the transducer further comprises a first electrical conductor configured to make electrical contact with the first surface of the transducer and a second electrical conductor configured to make electrical contact with the second surface of the transducer; and wherein the transducer has an outline that is within the perimeter; and wherein the first electrical conductor and the second electrical conductor both extend beyond the outline in the same direction and are separated laterally with respect to the planar layer of the transducer such that the first electrical conductor and the second electrical conductor do not overlap in a direction perpendicular to the planar layer of the transducer; and wherein at least a portion of one of the two polymer sheets includes a window in a portion of the foil between the outline and the perimeter for making electrical contact with the first electrical conductor and with the second electrical conductor.

23. Method of attaching the portion of the foil within the perimeter of claim 1 to an article such as a medical device or a medical needle; the method comprising the steps of:

either:

pressing an article into the adhesive layer; and pulling the article away from the carrier substrate such that the portion of the foil within the perimeter is separated from the carrier substrate and remains attached to the article;

or:

rolling an article along the surface of the adhesive layer such that the portion of the foil within the perimeter is separated from the carrier substrate and remains attached to the article.

\* \* \* \* \*